United States Patent [19]

De Gregorio

[11] Patent Number: 5,176,714
[45] Date of Patent: Jan. 5, 1993

[54] METHOD OF TREATING CONTACT LENSES

[75] Inventor: Mauro De Gregorio, Rome, Italy

[73] Assignee: Aziende Chimiche Riunite Angelini Francesco A.C.R.A.F. S.p.A., Rome, Italy

[21] Appl. No.: 429,179

[22] Filed: Oct. 30, 1989

Related U.S. Application Data

[60] Division of Ser. No. 296,275, Jan. 11, 1989, Pat. No. 4,895,676, Continuation of Ser. No. 77,620, Jul. 24, 1987, abandoned.

[30] Foreign Application Priority Data

Aug. 1, 1986 [IT]  Italy ............................. 21384 A/86

[51] Int. Cl.⁵ ..................... C11D 3/14; D06M 16/00
[52] U.S. Cl. ................ 252/174.12; 252/542; 252/DIG. 12; 424/429; 435/264; 514/839

[58] Field of Search ............ 252/542, 174.12; 514/407, 839, 840; 8/507; 435/264; 422/28; 424/429

[56] References Cited

U.S. PATENT DOCUMENTS

| | | | |
|---|---|---|---|
| Re. 32,672 | 5/1988 | Huth et al. | 252/174.12 |
| 4,451,477 | 5/1984 | Silvestrini et al. | 424/273 N |
| 4,832,754 | 5/1989 | Trumpower | 252/174.12 |
| 4,921,630 | 5/1990 | Bhatia | 252/174.12 |

*Primary Examiner*—Jack Cooper
*Assistant Examiner*—John F. McNally
*Attorney, Agent, or Firm*—Ladas & Parry

[57] ABSTRACT

Treatment of contact lenses by an effective amount of bendazac, 5-hydroxybendazac or a salt thereof with a physiologically acceptable base.

3 Claims, No Drawings

METHOD OF TREATING CONTACT LENSES

This is a divisional of copending application Ser. No. 7/296,275 filed on Jan. 11, 1989 now U.S. Pat. No. 4,895,676 which is a continuation application of Ser. No. 07/077,620 filed on Jul. 24, 1987 (now abandoned).

This invention relates to a method of treating contact lenses.

More particularly, it relates to the use of compounds which inhibit proteins sedimentation from lacrimal fluid on contact lenses, preferably of the soft type, and neutralize possible proteins sediments without substantially affecting mucus secretion by mucous membranes.

It is known that soft contact lenses represent a progress in comparison with rigid ones in that they do not cause and do not transmit mechanical traumas to the eye. Nevertheless, they have the drawback of quickly undergoing opaqueness because of protein sediments from lacrimal fluid, the amount and nature of which are widely different from individual to individual. Moreover, very often, the said protein sediments promote a keratoconjuctival process of sensitization which causes corneal irritation phenomena.

Several washing techniques have been suggested for removing the above said sediments, preferably by means of solutions containing surfactants or enzymes.

These techniques, however, do not allow removing all the sediments and leave some residue which causes the above mentioned drawbacks.

Therefore, a compound is still in great demand capable of completely, or to a great extent, preventing the formation of protein sediments on contact lenses and which anyhow is capable of preventing the small sediment, so formed, from having sensitization properties.

It has been now found that the so called "Aspirin-like" compounds, that is the non-steroid antiinflammatory acid compounds, such as salicylic acid, phenylbutazone, ibuprofen and mefenamic acid, posses such properties.

These compounds, however, substantially reduce the amount of mucus secreted by mucous membranes. Since mucus plays a very important role in protecting the eye, the so called "Aspirin-like" compounds result to be contraindicated for contacting the eye.

Furthermore, it has been now surprisingly found that bendazac, 5-hydroxy-bendazac and their salts with inorganic or organic physiologically acceptable bases, inhibit sedimentation of proteins from lacrimal fluid on contact lenses and neutralize the irritative properties of possible protein sediments without substantially affecting the secretion of mucus by mucous membranes.

It is, therefore, an object of this invention to provide a method of treating contact lenses, preferably of the soft type, comprising contacting a lens with an effective amount of bendazac, 5-hydroxy-bendazac or a salt thereof with an organic or inorganic physiologically base.

The compounds of formula:

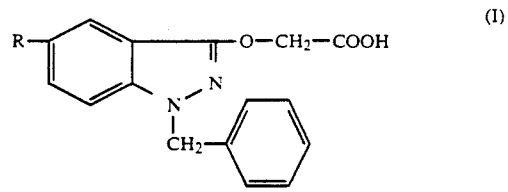

where R is H (bendazac) or OH (5-hydroxy-bendazac), and their salts with inorganic and organic physiologically acceptable bases, are already known, for example from the Italian patent application Nr. 49,790 A/81 of Nov. 27, 1981 and European patent application Nr. 191,520 of Jan. 29, 1986 that describe their use as anticataract agents.

Examples of suitable bases are the alkali metals such as sodium and potassium, the aliphatic amines, the basic aminoacids such as lysine and arginine, and the like.

Before being contacted with the lens, a compound of formula I or a physiologically acceptable salt thereof is preferably dissolved into a liquid.

The contact time of the solution comprising a compound of formula I or a physiologically acceptable salt thereof with a lens shall, of course, vary depending on the compound and the type of solution used. For instance, such time will be at least one hour in the case of deterging or wetting solutions, whereas it will be a few minutes in the case of rinsing solutions.

Another object of this invention is to provide the use of a compound of formula I or of a physiologically acceptable salt thereof for preparing solutions for the treatment of contact lenses.

The said solutions are prepared by dissolving a compound of formula I or a physiologically acceptable salt thereof in a non-toxic solvent which is compatible with both the said compound and the lens and which is suitable for undergoind sterilization. Preferably, the said solvent consists of purified or distilled sterile water.

The solutions of this invention may also comprise other ingredients, the nature and amount of which vary depending on the type of solution to be prepared; this may indeed be of a wetting, deterging, disinfecting or rinsing type.

In the case of individuals in which the compound of formula I used or its physiologically acceptable salt is not capable of inhibiting up to 100% of the formation of protein sediments, the solutions prepared according to this invention are used together with solutions comprising surfactants or enzymes, or they themselves comprise surfactants and/or enzymes. However the time for becoming opaque is much longer in the case of the lens thus treated than that observed, for the same individual, when the lens is treated with surfactants and/or enzymes alone and even the probability of the arising of corneal irritation is very reduced compared to that of the usual treatments.

Examples of other suitable ingredients are preservatives, salts for regulating the osmotic pressure, antiseptics, disinfectants, antioxidants and buffers.

Said solutions may be easily prepared according to usual techniques which are well known to the people skilled in this art and comprise simple operations such as dissolving and sterilization.

A further object of this invention is to provide aqueous solutions comprising an effective amount of a compound of formula I or of a physiologically acceptable salt thereof, which are suitable for wetting, deterging or rinsing contact lenses.

Typical examples of solutions according to this invention comprise a compound of formula I or a physiologically acceptable salt thereof and at least a disinfectant, a surfactant and/or an enzyme.

Examples of suitable disinfectants, surfactants and enzymes are chlorhexidine gluconate, octylphenoxyoctanol and papain, respectively.

Preferably the solutions according to this invention comprise from 0.05 to 2% of bendazac, or of 5-hydroxybendazac, or the corresponding amount of a salt with a physiologically acceptable organic or inorganic base.

The following examples are given to illustrate this invention without, however, limiting it in any way.

| 100 mL contain: | |
|---|---|
| EXAMPLE 1 | |
| Wetting solution | |
| Bendazac sodium salt | 0.25 g |
| Hydroxy ethyl cellulose | 0.4 g |
| Polyvinyl alcohol | 1.4 g |
| Thymerosal | 0.004 g |
| Sodium edetate | 0.20 g |
| Sodium chloride | 0.75 g |
| Boric acid or borax to | pH 7.4 |
| Sterile distilled water q.s. to | 100 ml |
| EXAMPLE 2 | |
| Wetting solution | |
| 5-hydroxybendazac | 0.25 g |
| Hydroxy ethyl cellulose | 0.4 g |
| Polyvinyl alcohol | 1.4 g |
| Thymerosal | 0.004 g |
| Sodium edetate | 0.20 g |
| Sodium chloride | 0.65 g |
| Anhydrous Sodium sulfite | 0.15 g |
| 1 N Sodium hydroxide to | pH 6.5 |
| Sterile distilled water q.s. to | 100 ml |
| EXAMPLE 3 | |
| Deterging solution | |
| Bendazac sodium salt | 0.25 g |
| Polyvinyl alcohol | 1.4 g |
| Thymerosal | 0.004 g |
| Sodium edetate | 0.20 g |
| Sodium chloride | 0.75 g |
| Octyl phenoxy ethanol | 0.35 g |
| Boric acid or borax to | pH 7.4 |
| Sterile distilled water q.s. to | 100 ml |
| EXAMPLE 4 | |
| Deterging solution | |
| 5-hydroxybendazac | 0.25 g |
| Polyvinyl alcohol | 1.4 g |
| Thymerosal | 0.004 g |
| Sodium edetate | 0.20 g |
| Sodium chloride | 0.65 g |
| Anhydrous Sodium sulfite | 0.15 g |
| Octyl phenoxy ethanol | 0.35 g |
| 1 N Sodium hydroxide to | pH 6.5 |
| Sterile distilled water q.s. to | 100 ml |
| EXAMPLE 5 | |
| Disinfecting solution | |
| Bendazac sodium salt | 0.25 g |
| Sodium chloride | 0.75 g |
| Thymerosal | 0.001 g |
| Chlohrexidine gluconate | 0.005 g |
| Sodium edetate | 0.1 g |
| Polysorbate 80 | 0.05 g |
| Boric acid or borax to | pH 7.4 |
| Sterile demineralized water q.s. to | 100 ml |
| EXAMPLE 6 | |
| Disinfecting solution | |
| 5-hydroxybendazac | 0.25 g |
| Sodium chloride | 0.65 g |
| Anhydrous Sodium sulfite | 0.15 g |
| Thymerosal | 0.001 g |
| Chlohrexidine gluconate | 0.005 g |
| Sodium edetate | 0.1 g |
| Polysorbate 80 | 0.05 g |
| Sterile demineralized water q.s. to | 100 ml |
| EXAMPLE 7 | |

| 100 mL contain: | |
|---|---|
| Solution for rinsing or thermal disinfection | |
| Bendazac | 0.25 g |
| Sodium chloride | 0.75 g |
| Thymerosal | 0.001 g |
| Sodium edetate | 0.1 g |
| Boric acid or borax to | pH 7.4 |
| Sterile demineralized water q.s. to | 100 ml |
| EXAMPLE 8 | |
| Solution for rinsing or thermal disinfection | |
| 5-hydroxybendazac | 0.25 g |
| Sodium chloride | 0.65 g |
| Anhydrous Sodium sulfite | 0.15 g |
| Thymerosal | 0.001 g |
| Sodium edetate | 0.1 g |
| 1 N Sodium hydroxide to | pH 6.5 |
| Sterile demineralized water q.s. to | 100 ml |
| EXAMPLE 9 | |
| Wetting solution | |
| Bendazac Lysinate | 0.4 g |
| Hydroxy ethyl cellulose | 0.4 g |
| Polyvinyl alcohol | 1.4 g |
| Thymerosal | 0.004 g |
| Sodium edetate | 0.2 g |
| Sodium chloride | 0.75 g |
| Boric acid or borax to | pH 7.4 |
| Sterile distilled water q.s. to | 100 ml |

A first experiment has been carried out on six individuals wearing soft contact lenses and specifically selected because they produced every 5-6 days such an amount of sediments on the said lenses that they had to treat their lenses daily with a deterging composition containing a surfactant, and weekly with a composition containing a proteolytic enzyme.

These individuals stopped using the composition containing a proteolytic enzyme. For a period of three months they regularly dipped their lenses in a solution according to example 9 every night after the usual deterging and disinfecting treatment. More particularly, the lenses were kept in the above solution overnight.

In the course of the entire three months period, all six individuals did not need to clean their lenses with any composition containing a proteolytic enzyme.

A second experiment has been carried out on ten individuals whose soft contact lenses showed appreciable sediments easily detectable, observing the lenses on a black background through a 7-fold magnification. These individuals used the solution according to example 9 by contacting directly the worn lenses in situ with two drops of the said solution 4 times a day.

The regular use of the said solution for 14 consecutive days caused, in all ten individuals, disappearance or substantial reduction of the sediments on the lenses.

I claim:

1. A contact lens aqueous treating solution comprising bendazac, 5-hydroxy-bendazac, or salt thereof with an inorganic or organic physiologically acceptable base said bendazac, 5-hydroxy-bendazac or salt thereof present in an amount effective for inhibiting protein sedimentation from lacrimal fluid on said contact lens and for neutralizing irritative effects of existing protein sediments without substantially affecting mucus secretion by mucous membranes of the contact lens wearer said solution further comprising an enzyme effective to aid in the inhibition or neutralization of said protein sedimentation.

2. The aqueous solution according to claim 1, which comprises from 0.05 to 2% of bendazac, or of 5-hydroxybendazac, or the corresponding amount of a salt thereof with an organic or inorganic physiologically acceptable base.

3. The aqueous solution, as in claim 1 wherein the enzyme is papain.

* * * * *